(12) United States Patent
McLean et al.

(10) Patent No.: US 7,059,858 B2
(45) Date of Patent: *Jun. 13, 2006

(54) UNIVERSAL TRAY DESIGN HAVING ANATOMICAL FEATURES TO ENHANCE FIT

(75) Inventors: Bruce S. McLean, Sandy, UT (US); Dan E. Fischer, Sandy, UT (US); Peter M. Allred, Riverton, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/783,597

(22) Filed: Feb. 19, 2004

(65) Prior Publication Data

US 2005/0186539 A1 Aug. 25, 2005

(51) Int. Cl.
*A61C 15/00* (2006.01)
(52) U.S. Cl. .................................. 433/216; 433/80
(58) Field of Classification Search .................. 433/6, 433/41, 43, 80, 215, 216; 128/861
See application file for complete search history.

(56) References Cited

U.S. PATENT DOCUMENTS

| 165,584 | A | 7/1875 | Hopfen |
| 1,637,153 | A | 7/1927 | Lawton |
| 2,257,709 | A | 9/1941 | Anderson |
| 2,835,628 | A | 5/1958 | Saffir ............................ 167/84 |
| 3,319,626 | A | 5/1967 | Lindsay |
| 3,339,547 | A | 9/1967 | Drabkowski |
| 3,527,219 | A | 9/1970 | Greenberg |
| 3,577,640 | A | 5/1971 | Lee ................................. 32/32 |
| 3,624,909 | A | 12/1971 | Greenberg |
| 3,625,215 | A | * | 12/1971 | Quisling ....................... 433/25 |
| 3,688,406 | A | 9/1972 | Porter et al. ................. 32/40 R |
| 3,955,281 | A | 5/1976 | Weitzman |
| 4,044,762 | A | 8/1977 | Jacobs ......................... 128/136 |
| 4,063,552 | A | 12/1977 | Going et al. ................. 128/136 |
| 4,064,628 | A | 12/1977 | Weitzman |
| 4,138,814 | A | 2/1979 | Weitzman |

(Continued)

FOREIGN PATENT DOCUMENTS

WO        WO 88/06869         9/1988

(Continued)

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com (Dec. 2003).

*Primary Examiner*—Cary E. O'Connor
(74) *Attorney, Agent, or Firm*—Workman Nydegger

(57) ABSTRACT

A tray-shaped dental treatment device includes a moisture-resistant barrier layer having a front side wall and a bottom wall, and a dental treatment composition. In addition, the tray-shaped dental treatment device includes at least one of the following anatomical features to enhance the fit of the device: (1) the bottom wall includes a plurality of cuts positioned to help the bottom wall better conform to abrupt changes in the diameters of a person's teeth where the bicuspids and canines meet, or (2) the bottom wall includes at least one V-shaped or U-shaped indentation configured to be inserted into the depression typically found along the top surfaces of a person's molars, or (3) the front side wall and bottom wall include radii of curvature that account for typical flaring of a patient's incisors.

34 Claims, 7 Drawing Sheets

U.S. PATENT DOCUMENTS

| | | | |
|---|---|---|---|
| RE33,093 E | 10/1989 | Schiraldi et al. ............. 424/676 |
| 4,900,721 A | 2/1990 | Bansemir et al. ............. 514/25 |
| 4,902,227 A | 2/1990 | Smith |
| 5,008,093 A | 4/1991 | Merianos .................... 423/272 |
| 5,051,476 A | 9/1991 | Uji et al. |
| 5,085,585 A | 2/1992 | Zimble |
| 5,108,742 A | 4/1992 | Merianos ................. 424/78.32 |
| 5,112,225 A | 5/1992 | Diesso ......................... 433/48 |
| 5,183,901 A | 2/1993 | Login et al. ................ 548/543 |
| 5,211,559 A | 5/1993 | Hart et al. |
| 5,310,563 A | 5/1994 | Curtis et al. ................ 424/616 |
| 5,326,685 A | 7/1994 | Gaglio et al. ............... 433/215 |
| 5,346,061 A | 9/1994 | Newman et al. ........... 206/221 |
| 5,356,291 A | 10/1994 | Darnell |
| 5,376,006 A | 12/1994 | Fischer |
| 5,425,953 A | 6/1995 | Sintov et al. ............... 424/404 |
| 5,462,067 A * | 10/1995 | Shapiro ...................... 128/861 |
| 5,562,449 A | 10/1996 | Jacobs et al. ............... 433/215 |
| 5,573,399 A | 11/1996 | McClintock, II |
| 5,575,654 A | 11/1996 | Fontenot |
| 5,611,687 A | 3/1997 | Wagner ........................ 433/80 |
| 5,616,027 A | 4/1997 | Jacobs et al. |
| 5,631,000 A | 5/1997 | Pellico ......................... 424/53 |
| 5,639,445 A | 6/1997 | Curtis et al. .................. 424/49 |
| 5,702,251 A | 12/1997 | McClintock, II |
| 5,707,235 A | 1/1998 | Knutson .................... 433/213 |
| 5,711,935 A | 1/1998 | Hill et al. ..................... 424/49 |
| 5,752,826 A | 5/1998 | Andreiko ...................... 433/41 |
| 5,769,633 A | 6/1998 | Jacobs et al. |
| 5,816,802 A | 10/1998 | Montgomery |
| 5,846,058 A | 12/1998 | Fischer ....................... 433/216 |
| 5,846,082 A | 12/1998 | Thornton |
| 5,851,512 A | 12/1998 | Fischer |
| 5,863,202 A | 1/1999 | Fontenot et al. |
| 5,879,691 A | 3/1999 | Sagel et al. ................. 429/401 |
| 5,891,453 A | 4/1999 | Sagel et al. ................. 424/401 |
| 5,894,017 A | 4/1999 | Sagel et al. ................. 424/401 |
| 5,895,218 A | 4/1999 | Quinn et al. |
| 5,922,307 A | 7/1999 | Montgomery ................ 424/53 |
| 5,924,863 A | 7/1999 | Jacobs et al. |
| 5,980,249 A | 11/1999 | Fontenot |
| 5,985,249 A | 11/1999 | Fischer |
| 5,989,569 A | 11/1999 | Dirksing et al. ............ 424/401 |
| 6,045,811 A | 4/2000 | Dirksing et al. ............ 424/401 |
| 6,080,397 A | 6/2000 | Pfirrmann ................ 424/78.08 |
| 6,089,869 A | 7/2000 | Schwartz |
| 6,096,328 A | 8/2000 | Sagel et al. ................. 424/401 |
| 6,106,293 A | 8/2000 | Wiesel ....................... 433/215 |
| 6,126,443 A | 10/2000 | Burgio |
| 6,136,297 A | 10/2000 | Sagel et al. ................... 424/49 |
| 6,142,780 A | 11/2000 | Burgio |
| 6,155,832 A | 12/2000 | Wiesel ....................... 433/215 |
| 6,183,251 B1 | 2/2001 | Fischer |
| 6,197,331 B1 | 3/2001 | Lerner et al. ............... 424/448 |
| 6,247,930 B1 | 6/2001 | Chiang et al. |
| 6,274,122 B1 | 8/2001 | McLaughlin |
| 6,277,458 B1 | 8/2001 | Dirksing et al. ............ 424/42.3 |
| 6,280,196 B1 | 8/2001 | Berghash |
| 6,287,120 B1 | 9/2001 | Wiesel ....................... 433/215 |
| 6,309,625 B1 | 10/2001 | Jensen et al. |
| 6,312,671 B1 | 11/2001 | Jensen et al. |
| 6,322,360 B1 | 11/2001 | Burgio ......................... 433/80 |
| 6,331,292 B1 | 12/2001 | Montgomery ................ 424/53 |
| 6,343,932 B1 | 2/2002 | Wiesel ....................... 433/215 |
| 6,364,665 B1 | 4/2002 | Trettenerp .................. 433/215 |
| 6,379,147 B1 | 4/2002 | Georgakis et al. ............ 433/37 |
| 6,419,903 B1 | 7/2002 | Xu et al. ....................... 424/49 |
| 6,419,906 B1 | 7/2002 | Xu et al. ....................... 424/53 |
| 6,435,873 B1 | 8/2002 | Burgio ......................... 433/80 |
| 6,440,396 B1 | 8/2002 | McLaughlin ................. 424/49 |
| 6,458,380 B1 | 10/2002 | Leaderman ................. 424/443 |
| 6,461,158 B1 | 10/2002 | Sagel et al. .................... 433/30 |
| 6,488,914 B1 | 12/2002 | Montgomery ................ 424/53 |
| 6,497,575 B1 | 12/2002 | Zavitsanos et al. ......... 433/215 |
| 6,500,408 B1 | 12/2002 | Chen ........................... 424/53 |
| 6,503,486 B1 | 1/2003 | Xu et al. ....................... 424/53 |
| 6,506,053 B1 | 1/2003 | Wiesel ....................... 433/215 |
| 6,514,483 B1 | 2/2003 | Xu et al. ....................... 424/53 |
| 6,514,484 B1 | 2/2003 | Rajaiah et al. ................ 424/53 |
| 6,551,579 B1 | 4/2003 | Sagel et al. .................... 424/53 |
| 6,649,147 B1 | 11/2003 | Ye et al. ....................... 424/49 |
| 6,682,721 B1 | 1/2004 | Kim et al. ..................... 424/53 |
| 6,689,344 B1 | 2/2004 | Chang et al. .................. 424/53 |
| 6,730,316 B1 | 5/2004 | Chen ......................... 424/435 |
| 6,840,771 B1 * | 1/2005 | Wagner ...................... 433/214 |
| 2001/0046654 A1 | 11/2001 | Zavitsanos et al. ........... 433/32 |
| 2002/0006387 A1 * | 1/2002 | Sagel et al. .................... 424/53 |
| 2002/0006388 A1 | 1/2002 | Sagel et al. .................... 424/53 |
| 2002/0012685 A1 | 1/2002 | Sagel et al. .................. 424/401 |
| 2002/0018754 A1 | 2/2002 | Sagel et al. .................... 424/49 |
| 2002/0081555 A1 | 6/2002 | Wiesel ....................... 433/215 |
| 2002/0164292 A1 | 11/2002 | Peterson et al. .............. 424/53 |
| 2002/0182154 A1 | 12/2002 | McLaughlin ................. 424/53 |
| 2002/0187111 A1 | 12/2002 | Xu et al. ....................... 424/53 |
| 2002/0187112 A1 | 12/2002 | Xu et al. ....................... 424/53 |
| 2003/0003421 A1 | 1/2003 | Besenheider et al. ....... 433/215 |
| 2003/0012747 A1 | 1/2003 | Peterson ...................... 424/53 |
| 2003/0036037 A1 | 2/2003 | Zavitsanos et al. ......... 433/215 |
| 2003/0044631 A1 | 3/2003 | Sagal et al. ................. 428/548 |
| 2003/0068284 A1 | 4/2003 | Sagel et al. .................... 424/53 |
| 2003/0068601 A1 | 4/2003 | Zavitsanos et al. ......... 433/215 |
| 2003/0082114 A1 | 5/2003 | Kim et al. ..................... 424/53 |
| 2003/0133884 A1 | 7/2003 | Chang et al. .................. 424/53 |
| 2003/0194382 A1 * | 10/2003 | Chang et al. .................. 424/53 |
| 2003/0198606 A1 | 10/2003 | Kim et al. ..................... 424/53 |
| 2004/0002035 A1 * | 1/2004 | Jacobs et al. ............... 433/215 |
| 2004/0214140 A1 * | 10/2004 | Fischer et al. .............. 433/215 |

FOREIGN PATENT DOCUMENTS

WO      WO 03/000216      1/2003

* cited by examiner

UNIVERSAL TRAY DESIGN HAVING ANATOMICAL FEATURES TO ENHANCE FIT

BACKGROUND OF THE INVENTION

1. The Field of the Invention

The present invention is in the field of dental tray shaped devices used to provide a desired dental treatment to a person's teeth. The device can be used for dental treatments such as bleaching, administration of fluoride, or application of other medicines.

2. The Relevant Technology

Virtually all people desire white or whiter teeth. To achieve this goal, people have veneers placed over their teeth or have their teeth chemically bleached. A common bleaching method involves the use of a dental tray that is custom-fitted to a person's teeth and that is therefore comfortable to wear. One type of customized tray is made from a stone cast of a person's teeth. Another is customized directly using a person's teeth as a template (e.g., "boil-and-bite" trays). Non-customized trays that approximate the shapes and sizes of a variety of users' dental arches have also been used. A dental bleaching composition is placed into the tray and the tray placed over the person's teeth for a desired period of time.

Another bleaching method involves painting a bleaching composition directly onto a person's teeth. A perceived advantage of paint-on bleaching is that it eliminates the need for a dental tray. The main disadvantage of a paint-on bleaching composition is that it remains directly exposed to the person's saliva and disruptive forces found in a person's mouth. As a result, a significant portion of the bleaching composition does not remain on the teeth where bleaching is desired. Some or all of the composition can dissolve away into the person's saliva and/or be transferred to adjacent oral tissues, potentially irritating soft oral tissues.

Another tooth bleaching method involves placing a flexible bleaching strip over a user's tooth surfaces. Conventional bleaching strips comprise a flexible plastic strip coated with a dental bleaching gel of moderate viscosity and relatively low stickiness on the side of the strip facing the user's teeth. To install the bleaching strip, a portion of the bleaching strip is placed over the front surfaces of the user's teeth, and the remainder is folded around the occlusal edges of the teeth and against a portion of the lingual surfaces. Like paint-on bleaching compositions, this procedure does not require the use of dental trays. Unlike paint-on bleaching compositions, bleaching strips include a plastic barrier that, at least in theory, keeps the dental bleaching gel from diffusing into the user's mouth.

In reality, because of the generally poor adhesion of bleaching strips to the user's teeth, coupled with their generally flimsy nature, it is often difficult for the user to maintain the bleaching strip in its proper position for the recommended time. Conventional bleaching strips are prone to slip off the teeth as a result of even minimal movement of the user's mouth, jaw or tongue. Indeed, it is recommended that the user not eat, drink, smoke or sleep while wearing the bleaching strip. In practice, it is difficult to talk or smile while properly maintaining the bleaching strip in the correct position.

Even if a user successfully maintains a conventional bleaching strip in its proper position during the recommended bleaching period, the bleaching gel often diffuses into the person's saliva, potentially causing a poor taste in the user's mouth and possibly discomfort to soft oral and throat tissues. The tendency of the bleaching gel to diffuse into the user's mouth can be accelerated through even minimal shifts of the bleaching strip over the user's teeth, with each shift potentially causing bleaching gel that remains adhered to the user's teeth, but not covered by the plastic strip, to be exposed to saliva in the user's mouth. In some cases, the bleaching strip can become so dislodged or mangled that it must be removed by the user and replaced with a fresh bleaching strip to complete the recommended bleaching time. This multiplies the cost and hassle of using conventional bleaching strips.

In practical terms, the use of conventional bleaching strips can greatly inhibit even the simplest of activities that involve movement of the user's mouth or tongue, such as talking, smiling, making other facial expressions, or even swallowing (which normally occurs subconsciously throughout the day). Indeed, the time when a person's mouth and tongue are the least prone to move is at night while the person is sleeping. Unfortunately, it is recommended that conventional bleaching strips not be used while sleeping, presumably to prevent accidental choking on an inadvertently dislodged bleaching strip. This confirms the tendency of conventional bleaching strips to easily dislodge from a user's teeth.

Ultimately, the main impediment to successful bleaching is the failure of users to complete the prescribed bleaching regimen. If the bleaching apparatus is difficult to install over a person's teeth, requires numerous repetitions to achieve observable results, or is uncomfortable to wear, the user may simply give up and prematurely abort the prescribed bleaching regimen. Thus, even if dental bleaching is possible using a particular bleaching apparatus or method, it is less likely to occur if the inadequacies of the bleaching apparatus or method cause a user to become discouraged before desired results are attained.

In view of the foregoing, there is an ongoing need for improved bleaching apparatus and methods that are simple and easy to use and that reliably remain in position over the user's teeth so as to reduce diffusion of bleaching composition into a user's oral cavity. Such improvements would be expected to improve or encourage compliance by the user.

BRIEF SUMMARY OF THE PREFFERED EMBODIMENTS

The present invention generally relates to improved dental treatment devices used to treat (e.g., bleach) a person's teeth. The inventive tray-shaped device includes a front side wall and a bottom wall. In addition, the tray-shaped device includes at least one of the following features to enhance anatomical fit: (1) the bottom wall includes a plurality of cuts positioned to help the bottom wall better conform to abrupt changes in the diameters of a person's teeth, particularly where the bicuspids and canines meet, (2) the bottom wall includes at least one V-shaped or U-shaped indentation configured to be inserted into the depression typically found along the top surfaces of a person's molars, and (3) the front and bottom wall include radii of curvature that account for typical flaring of a patient's incisors.

In one embodiment of a treatment device according to the invention, the bottom wall includes a cut on either side of the device approximately corresponding to the intersection of a person's canines and bicuspids. The cuts help to compensate for the fact that bicuspids are significantly thicker than canines by allowing for an abrupt discontinuity in the bottom wall of the treatment device. Without these cuts the bottom wall would be harder to conform to the canines since the adjacent bicuspids would tend to push the bottom wall away from the canines, thus potentially dislodging the bottom wall in this region. These and any other cuts within the bottom wall may also help compensate for differences between the inner and outer radii of the dental arch generally defined by the inner and outer tooth surfaces.

In another embodiment of a treatment device according to the invention, the bottom wall may include V-shaped or U-shaped indentations in the region of a person's molars that cause the bottom wall to better conform to the depression normally found in molars. In the absence of such V-shaped or U-shaped indentations, the bottom wall of the treatment device may have a tendency to span the molars like a bridge between the generally higher outer edges, thereby leaving a gap between the bottom wall and the surface of the molars between the outer edges. Permitting such a gap may inhibit or prevent bleaching the depressed molar surfaces. Moreover, a bottom wall that is stretched between the outer surfaces so as to leave a gap over the molar depressions may result in inadvertent dislodgment of the treatment device when the upper and lower molars are brought together. For example, if the bottom wall of a treatment device is pushed into the molar depression by the opposing molars, the front and/or bottom side walls may be pulled down across the tooth surfaces to compensate for this effective lengthening of the bottom wall in the vicinity of the molars.

In another embodiment of a treatment device according to the invention, the front and bottom walls may have different radii in order to compensate for the general flaring out of a person's incisors toward the incisal edges. Due to such flaring the diameter of a person's dental arch at the incisal edges is generally greater than the diameter at the gingival margin. Thus the part of the treatment device corresponding to the incisal edges near a person's incisors may advantageously have a larger radius than the part of the treatment device corresponding to the gingival margin. This helps provide better fit of the treatment device over a person's tooth surfaces.

The treatment composition may comprise various forms. According to one embodiment, the treatment composition comprises a single continuous bead or layer adjacent to at least a portion of an inner surface of a barrier layer. The treatment composition may comprise a sticky viscous gel, a less viscous gel, a highly viscous putty, or a substantially solid composition that is less adhesive prior to being moistened with saliva or water but that becomes more sticky and adhesive when moistened.

In another embodiment, the treatment device includes a layer or region of a substantially solid adhesive composition and a treatment gel or composition adjacent to at least one of the barrier layer or adhesive composition. The adhesive composition may, in some cases, be formulated so as to provide the same treatment as the separate treatment composition, a different treatment, or no treatment. It may provide a protective barrier between the active agent in the treatment composition or gel and the person's gums. It may include a bleaching agent activator in the case where the treatment composition includes a bleaching agent.

According to one embodiment, the tray-shaped device includes a barrier layer made of a moisture resistant material. According to one embodiment, the barrier layer comprises a thin, flexible membrane formed from a moisture-resistant polymer material. It is within the scope of the invention to provide barrier layers having any desired thickness or rigidity. In one embodiment, the barrier layer comprises a mixture of ethyl vinyl acetate and polypropylene.

The treatment and/or adhesive compositions may include any desired active agent, including, but not limited to, dental bleaching agents, desensitizing agents, remineralizing agents, antimicrobial agents, antiplaque agents, anti-tartar agents, or other medicaments. They also include at least one tissue adhesion agent. A non-limiting example of a suitable tissue adhesion agent is polyvinyl pyrrolidone (PVP). The treatment and/or adhesive: compositions may include other components as desired to yield a final composition having desired properties. Examples of other components include, but are not limited to, plasticizers and humectants (e.g., glycerin, sorbitol, and polyethylene glycol), volatile solvents (e.g., water and alcohols), bleaching agent stabilizers (e.g., EDTA and alkyl sulfates), bleaching agent activators (e.g., metals and metal compounds), neutralizing agents, thickening agents (e.g., fumed silica), flavorants, sweeteners, and the like.

The size and shape of the treatment devices according to the invention can be tailored to readily fit a person's upper or lower dental arch. They may also be tailored to fit person's having differently sized or shaped dental arches. The treatment devices are advantageously designed so as to substantially cover the front and lingual surfaces of the teeth and/or gums to be treated. The treatment devices are advantageously flexible and adhesive so as to readily conform to a wide variety of differently-sized teeth and dental arches.

The treatment devices according to the invention can be designed to be worn for any desired time period. Increasing the concentration of active agent used generally reduces the required treatment time. Nevertheless, due to the extremely comfortable fit between the inventive treatment devices and the person's teeth, it is possible to wear such devices for extended periods of time. Treatment devices according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional bleaching strips, which do not reliably adhere to teeth, or intrusive bleaching devices such as large, bulky bleaching dental appliances.

The treatment devices can be designed to be worn for as little as a few minutes or as long as several hours. By way of example, not limitation, a typical treatment session of fast duration may last from about 10 to about 30 minutes. A treatment session of intermediate duration may last from about 30 minutes to about 2 hours. A treatment session of long duration, including professional or overnight treatment while a person is sleeping, may last from about 2 hours to about 12 hours. Treatment sessions may be repeated as many times as are needed to obtain a desired result. In the case of tooth bleaching, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

According to one embodiment, the treatment device may include an associated supporting structure, such as an exoskeleton, prior to use. An exoskeleton may be particularly useful where the barrier layer is very thin and flexible. The exoskeleton may have the same configuration as the treatment device so as to receive and support the front and bottom walls of the treatment device. The exoskeleton can provide additional support and ease of placement to the treatment device while positioning the device over a person's teeth. In one embodiment, the exoskeleton includes a handle to facilitate gripping and maneuverability of the exoskeleton while placing the treatment device over the teeth. Once positioned, the exoskeleton can be removed so as to leave the treatment device in place over the teeth.

For convenience of use, multiple treatment devices may be packaged together and sold as a kit. In one embodiment, the number of treatment devices provided with each kit can equal the number of sessions that represent a prescribed treatment regimen. The treatment devices can be sealed collectively or individually as desired. They may contain a removable protective layer on their interior surfaces to protect the treatment and/or adhesive composition from contamination or moisture. It is within the scope of the invention to provide a treatment composition that is initially separate from a barrier layer in the shape of a treatment device and that is applied onto the barrier layer by the end user.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1A:
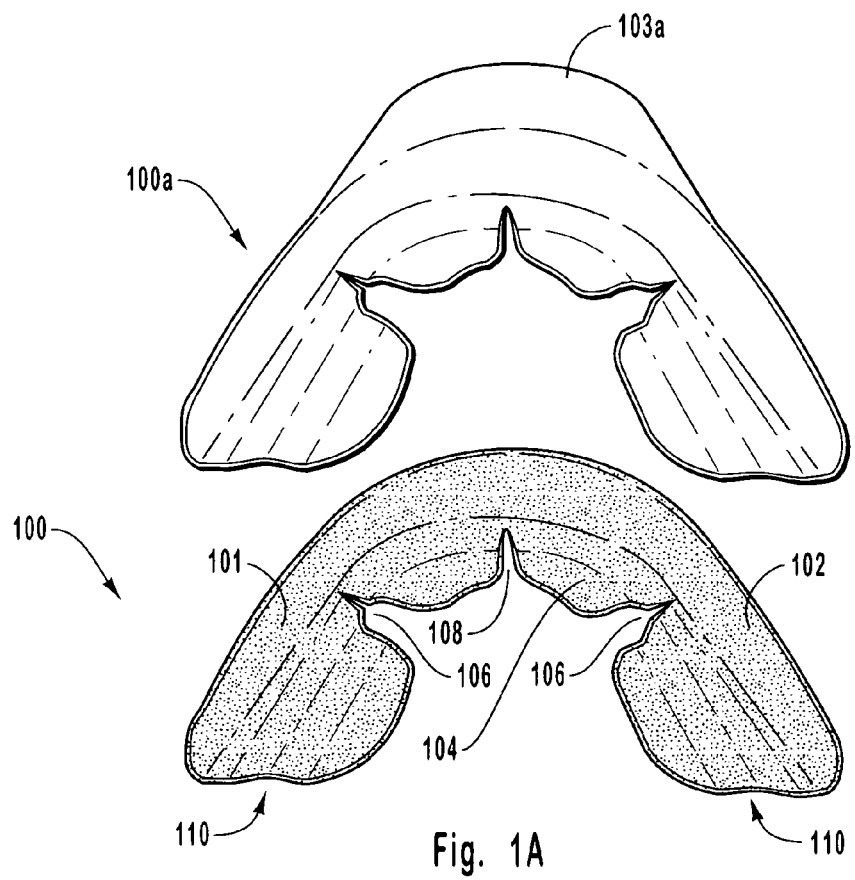
FIG. 1A is a perspective view of an exemplary tray-shaped dental treatment device configured to fit over at least a portion of a person's upper dental arch, next to an associated exoskeleton.

The inventive tray-shaped dental treatment device includes a moisture-resistant barrier layer having a front side wall and a bottom wall, and a dental treatment composition. In addition, the tray-shaped dental treatment device includes at least one of the following anatomical features to enhance the fit of the device: (1) the bottom wall includes a plurality of cuts positioned to help the bottom wall better conform to abrupt changes in the diameters of a person's teeth, particularly where the bicuspids and canines meet, (2) the bottom wall includes at least one V-shaped or U-shaped indentation configured to be inserted into the depression typically found along the top surfaces of a person's molars, and (3) the front and bottom wall include radii of curvature that account for typical flaring of a patient's incisors.

The term "barrier layer", as used herein, refers to one or more layers of a moisture-resistant material that protect the treatment composition and/or adhesive composition layer from ambient moisture and saliva found within a person's mouth when the tray-shaped dental treatment device is placed over the person's teeth. The barrier layer may also serve to protect the treatment composition and/or adhesive composition from moisture or other contaminants during storage and prior to use. The barrier layer may be in any desired form including, but not limited to, a sheet laminated to a surface of the treatment and/or adhesive composition, a coating applied to the treatment and/or adhesive composition, or a dental treatment tray.

The term "substantially solid," as used herein, refers to a composition that is in a solid or semi-solid condition. One characteristic of "substantially solid" adhesive compositions according to the invention is that they become more adhesive when an exposed surface thereof is moistened with, e.g., saliva or water. When moistened, the surface of the adhesive composition turns into a sticky material that is able to more strongly adhere to teeth compared to a substantially solid adhesive composition that has not been moistened. The composition at the surface may become a viscous liquid, paste or gel, at least temporarily, depending on the amount of moisture that is applied to the surface of the "substantially solid" adhesive composition. Nevertheless, the consistency of the moistened surface can remain "substantially solid" depending on the degree of initial moistening, or it can stiffen and even revert back to being "substantially solid" as the initial quantity of surface moisture diffuses into a remaining portion of the "substantially solid" adhesive composition over time (e.g., during a bleaching procedure in which the composition is protected from saliva and ambient moisture in a person's mouth by a moisture-resistant barrier layer).

The term "molecular weight", as used herein, refers to number average molecular weight expressed in Daltons unless otherwise specified.

II. Exemplary Tray-Shaped Dental Treatment Devices

A. Barrier Layer

The tray-shaped dental treatment device includes a barrier layer. According to one embodiment of the invention, the barrier layer comprises a thin, flexible membrane formed from a moisture-resistant polymer material. In a preferred embodiment, the barrier layer comprises a thin, flexible layer of a mixture of ethyl vinyl acetate and polypropylene.

According to another embodiment, it may be formed of a polyolefin or similarly moisture-resistant material, such as wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes or polyesteramides. Examples of suitable polyolefins for use in making the barrier layer include, but are not limited to, polyethylene (PE), high density polyethylene (HDPE), low density polyethylene (LDPE), ultra low density polyethylene (ULDPE), polypropylene, and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. Plasticizers, flow additives, and fillers known in the art can be used as desired to modify the properties of any of the foregoing polymers used to form the barrier layer.

B. Dental Treatment Compositions

The dental treatment composition may comprise various forms. According to one embodiment, the treatment composition comprises a single continuous bead or layer adjacent to at least a portion of an inner surface of the barrier layer. The treatment composition may comprise a sticky viscous gel, a less viscous gel, a highly viscous putty, or a substantially solid adhesive composition that is less adhesive prior to being moistened with saliva or water but that becomes more sticky and adhesive when moistened.

The treatment composition may comprise various forms. According to one embodiment, the treatment composition comprises a single continuous bead or layer adjacent to at least a portion of an inner surface of a barrier layer. The treatment composition may comprise a sticky viscous gel, a less viscous gel, a highly viscous putty, or a substantially solid composition that is less adhesive prior to being moistened with saliva or water but that becomes more sticky and adhesive when moistened.

In one embodiment, the treatment device includes a layer or region of a substantially solid adhesive composition and a treatment gel or putty adjacent to at least one of the barrier layer or adhesive composition. The adhesive composition may, in some cases, be formulated so as to provide the same treatment as the separate gel or putty treatment composition, a different treatment, or no treatment. It may provide a protective barrier between the active agent in the gel or putty and the person's gums. It may include a bleaching agent activator in the case where the gel or putty includes a bleaching agent.

Prior to being moistened in preparation for or during use, the substantially solid adhesive composition comprises a substantially solid composition. The adhesive composition may comprise a single coherent mass or region, or it may comprise a plurality of coherent masses or regions of a substantially solid adhesive composition. Providing a substantially solid and coherent adhesive composition better maintains the tray-like treatment device against the teeth being bleached. This, in turn, promotes better tooth whitening and reduces irritation to surrounding oral tissues.

The dental treatment compositions include at least one tissue adhesion agent, and may include an optional active agent. Following are examples of tissue adhesion agents and optional active agents.

1. Tissue Adhesion Agents

The tissue adhesion agent may comprise any known tackifying agent that is substantially non-adhesive, or less adhesive, when treatment composition is substantially solid but which becomes more adhesive to teeth when the treatment composition is moistened with, e.g., water or saliva. A presently preferred tissue adhesion agent is polyvinyl pyrrolidone (PVP). Examples of other suitable tissue adhesion agents include carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like. Characteristics of substantially solid adhesive treatment compositions in particular, and these and other tissue adhesion agents are disclosed in U.S. patent application Ser. No. 10/446,235, filed May 27, 2003, and titled TRAY-LIKE DENTAL BLEACHING DEVICES HAVING A BARRIER LAYER AND A SUBSEQUENTLY SOLID BLEACHING COMPOSITION, and U.S. patent application Ser. No. 10/446,471, filed May 27, 2003, and titled SUBSTANTIALLY SOLID DENTAL BLEACHING COMPOSITION IN A TRAY-LIKE CONFIGURATION, both of which are hereby incorporated by reference with respect to their disclosure of substantially solid adhesive compositions and tissue adhesion agents.

The amount of tissue adhesion agent in the dental treatment composition often depends on whether the composition is a gel, a putty, or a substantially solid adhesive composition. According to one embodiment, the one or more tissue adhesion agents are included in an amount in a range of about 10% to about 90% by weight of the treatment composition (exclusive of any bound water or other solvent), more preferably in a range of about 20% to about 80% by weight of the treatment composition, and most preferably in a range of about 40% to about 75% by weight of the treatment composition.

2. Active Agents

One or more active agents may be included in the dental treatment composition. Examples of various active agents include dental bleaching agents, desensitizing agents, remineralizing agents, antimicrobial agents, antiplaque agents, anti-tartar agents, or other medicaments.

A common dental bleaching agent that is known to bleach teeth and that has been found to be safe for oral use is hydrogen peroxide. However, hydrogen peroxide does not itself exist free in nature, but only as an aqueous solution or as a complex. Preferred dental bleaching agents comprise complexes of hydrogen peroxide because they are more stable than aqueous hydrogen peroxide, which tends to be unstable when heated, especially when water is removed by evaporation.

Non-limiting examples of complexed hydrogen peroxide include carbamide peroxide and metal perborates. Other bleaching agents that can be used to bleach teeth include, but are not limited to, metal percarbonates, peroxides, chlorites, and hypochlorites, peroxy acids, and peroxy acid salts.

If present, the one or more bleaching agents are preferably included in an amount in a range of about 5% to about 80% by weight of the treatment composition, more preferably in a range of about 10% to about 60% by weight of the treatment composition, and most preferably in a range of about 20% to about 50% by weight of the treatment composition.

As mentioned, other optional active agents may be included. Examples of desensitizing agents include potassium nitrate, other potassium salts, citric acid, citrates, and sodium fluoride. These and other desensitizing agents are disclosed in U.S. patent application Ser. No. 10/637,237, filed Aug. 8, 2003, and titled SUBSTANTIALLY SOLID DESENSITIZING COMPOSITIONS AND DEVICES HAVING A TRAY-LIKE CONFIGURATION AND METHODS OF MANUFACTURING AND USING SUCH COMPOSITIONS AND DEVICES, which is hereby incorporated by reference with respect to its disclosure of desensitizing agents. Examples of remineralizing agents include sodium fluoride, stannous fluoride, sodium monofluorophosphate, and other fluoride salts. Examples of antimicrobial agents include chlorhexidine, triclosan, and tetracycline. Examples of antiplaque and anti-tartar agents include pyrophosphate salts. These and additional medicaments that may be included as optional active agents are disclosed in U.S. patent application Ser. No. 10/646,484, filed Aug. 22, 2003, and titled COMPOSITIONS AND DEVICES HAVING A TRAY-LIKE CONFIGURATION FOR DELIVERING A MEDICAMENT AND METHODS OF MANUFACTURING AND USING SUCH COMPOSITIONS AND DEVICES, which is hereby incorporated by reference with respect to its disclosure of active agents.

3. Other Components

The dental treatment composition may include other components as desired to yield a final composition having desired properties. Examples of other components include, but are not limited to, plasticizers and humectants (e.g., glycerin, sorbitol, and polyethylene glycol), volatile solvents (e.g., water and alcohols, such as ethanol), bleaching agent stabilizers (e.g., EDTA and alkyl sulfates), bleaching agent activators (e.g., metals and metal compounds) neutralizing agents (e.g., sodium hydroxide), thickening agents (e.g., fumed silica), flavorants, sweeteners, and the like.

Additional treatment compositions and their components are disclosed in U.S. patent application Ser. No. 10/701,788, filed Nov. 4, 2003, and titled PRE-SHAPED DENTAL TRAYS AND TREATMENT DEVICES AND METHODS THAT UTILIZE SUCH DENTAL TRAYS, and U.S. patent application Ser. No. 10/692,117, filed Oct. 22, 2003, and titled BLEACHING COMPOSITIONS AND DEVICES HAVING A SOLID ADHESIVE LAYER AND BLEACHING GEL ADJACENT THERETO, both of which are hereby incorporated by reference with respect to their disclosure of treatment compositions.

C. Characteristics of Tray-Shaped Dental Treatment Devices

The tray-shaped dental treatment devices include at least one of the following anatomical features to enhance the fit of the tray-shaped dental treatment device: (1) the bottom wall includes a plurality of cuts positioned to help the bottom wall better conform to abrupt changes in the diameters of a person's teeth, particularly where the bicuspids and canines meet, (2) the bottom wall includes at least one V-shaped or U-shaped indentation configured to be inserted into the depression typically found along the top surfaces of a person's molars, and (3) the front and bottom wall include radii of curvature that account for typical flaring of a patient's incisors.

FIG. 1A illustrates a perspective view of an exemplary tray-shaped dental treatment device 100, along with an associated exoskeleton 100*a* having a handle 103*a*. The device 100 of FIG. 1A is sized and configured for placement over a person's upper dental arch. In the illustrated embodiment, the tray-shaped dental treatment device includes a substantially solid adhesive composition 101 which covers all the interior surfaces of the front wall 102 and the bottom wall 104.

The bottom wall 104 includes a plurality of cuts positioned to help the bottom wall better conform to abrupt changes in the diameters of a person's teeth, particularly where the bicuspids and canines meet. The cuts help to compensate for the fact that bicuspids are significantly thicker than canines by allowing for an abrupt discontinuity in the bottom wall 104 of the treatment device 100. Without these cuts the bottom wall 104 would be harder to conform to the canines since the adjacent bicuspids would tend to push the bottom wall 104 away from the canines, thus potentially dislodging the bottom wall 104 in this region. These and any other cuts within the bottom wall 104 may also help compensate for differences between the inner and outer radii of the dental arch generally defined by the inner and outer tooth surfaces. The cuts in the bottom wall 104 may extend the full width of the bottom wall 104.

In the illustrated embodiment, the cuts comprise notches 106. Notches 106 allow the bottom wall 104 to more freely spread open or compress without catching or overlapping other portions of the bottom wall 104. Notches 106 are positioned to help the bottom wall better conform to abrupt changes in the diameter of a person's teeth, particularly where the bicuspids and the canines meet. In the illustrated embodiment, the vertex of each notch 106 initially opens at about 10°. Each notch 106 spreads substantially wider before reaching the inside edge of bottom wall 104. In the illustrated embodiment, except for the vertex, the notches 106 do not include any sharp corners. The corners are preferably rounded so as to provide a more comfortable fit.

The bottom wall also includes a notch 108 near the front of the bottom wall 104 of the device 100. Optional notch 108 allows the tray-shaped dental treatment device 100 to more easily spread open or compress in the area of the incisors. This is helpful in allowing the bottom wall 104 to more easily conform to differently-sized dental arches. As illustrated, notch 108 may also have rounded corners.

In the illustrated embodiment, the bottom wall 104 also includes two V-shaped indentations 110 configured to be inserted into the depression typically found along the top surfaces of a person's left and right molars. Such a feature provides a tray-shaped dental treatment device that better conforms to the person's teeth, resulting in a more comfortable fit, as further illustrated in FIG. 7A.

Figure 1B:
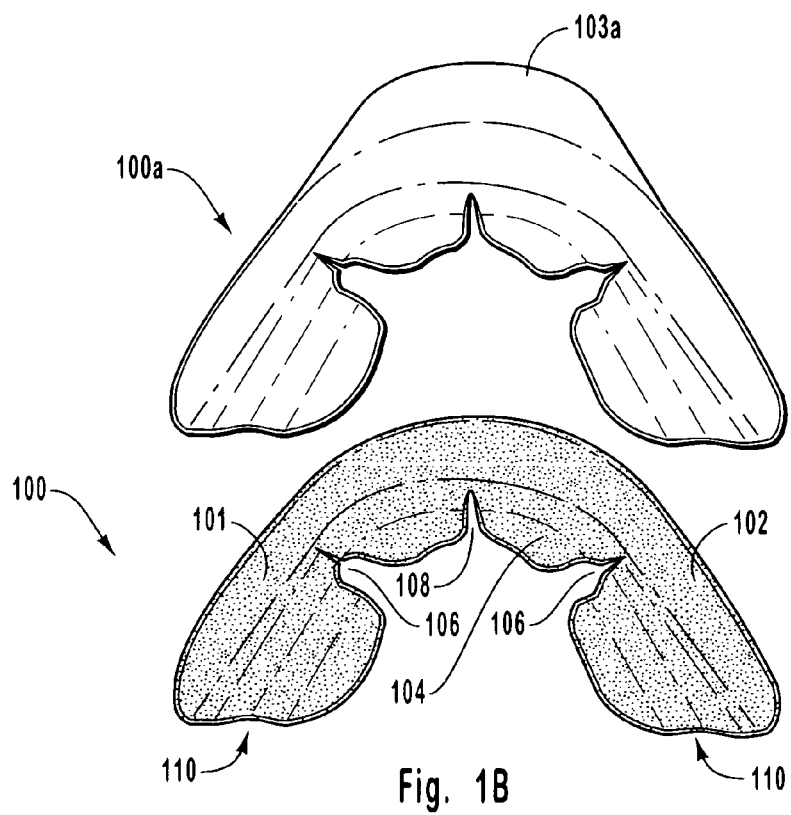
FIG. 1B is a perspective view of an exemplary tray-shaped dental treatment device configured to fit over at least a portion of a person's lower dental arch, next to an associated exoskeleton.

FIG. 1B illustrates a perspective view of an exemplary tray-shaped dental treatment device 100' along with an associated exoskeleton 100*a*' having a handle 103*a*'. The tray-shaped dental treatment device 100' is sized and configured for placement over a person's lower dental arch. In the illustrated embodiment, the tray-shaped dental treatment device 100' includes an adhesive composition 101'. The tray-shaped dental treatment device includes a barrier layer of moisture resistant material having a front side wall 102' and a bottom wall 104'. Bottom wall 104' includes notches 106' in the bottom wall 104' positioned so as to help the bottom wall 104' better conform to abrupt changes in the diameter of a person's teeth, particularly where the bicuspids and canines meet. Bottom wall 104' further includes optional notch 108', which allows the tray-shaped dental treatment device 100' to more easily spread open or compress in the area of the incisors so as to more easily conform to differently-sized dental arches. Finally, the bottom wall 104' also includes two V-shaped indentations 110' configured to be inserted into the depression typically found along the top surfaces of a person's left and right molars.

Figure 2:
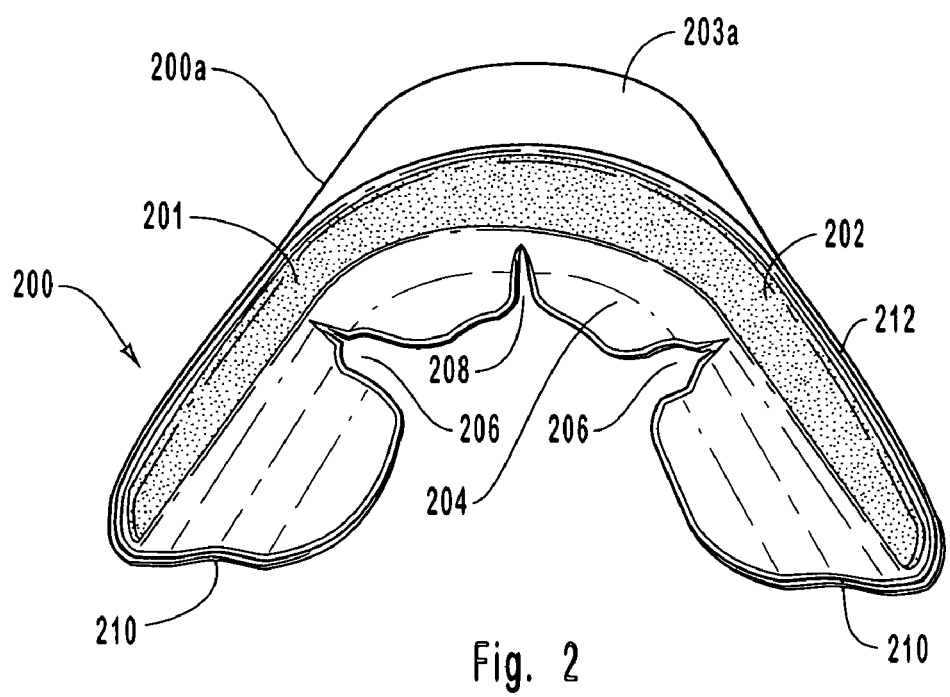
FIG. 2 is a perspective view of an exemplary tray-shaped dental treatment device comprising a barrier layer and a substantially solid adhesive composition placed within an exo-skeleton.

FIG. 2 illustrates a tray-shaped dental treatment device 200 having a moisture-resistant barrier layer 212 having a front side wall 202 and a bottom wall 204. The device 200 is held within exoskeleton 200a which includes a handle 203a for grasping and placing the device on one's teeth. The tray-shaped dental treatment device 200 also includes a substantially solid adhesive composition 201 covering the front side wall 202. The adhesive composition 201 includes an exterior surface disposed adjacent to an interior surface of the barrier layer 212 and an interior surface designed to directly contact a person's teeth when the tray-shaped dental treatment device 200 is in use.

Bottom wall 204 includes notches 206 in the bottom wall 204 positioned so as to help the bottom wall 204 better conform to abrupt changes in the diameter of a person's teeth, particularly where the bicuspids and canines meet. Bottom wall 204 also includes an optional notch 208, which allows the tray-shaped dental treatment device 200 to more easily spread open or compress in the area of the incisors so as to more easily conform to differently-sized dental arches. The bottom wall 204 also includes two V-shaped indentations 210 configured to be inserted into the depressions typically found along the top surfaces of a person's left and right molars.

Figure 3:
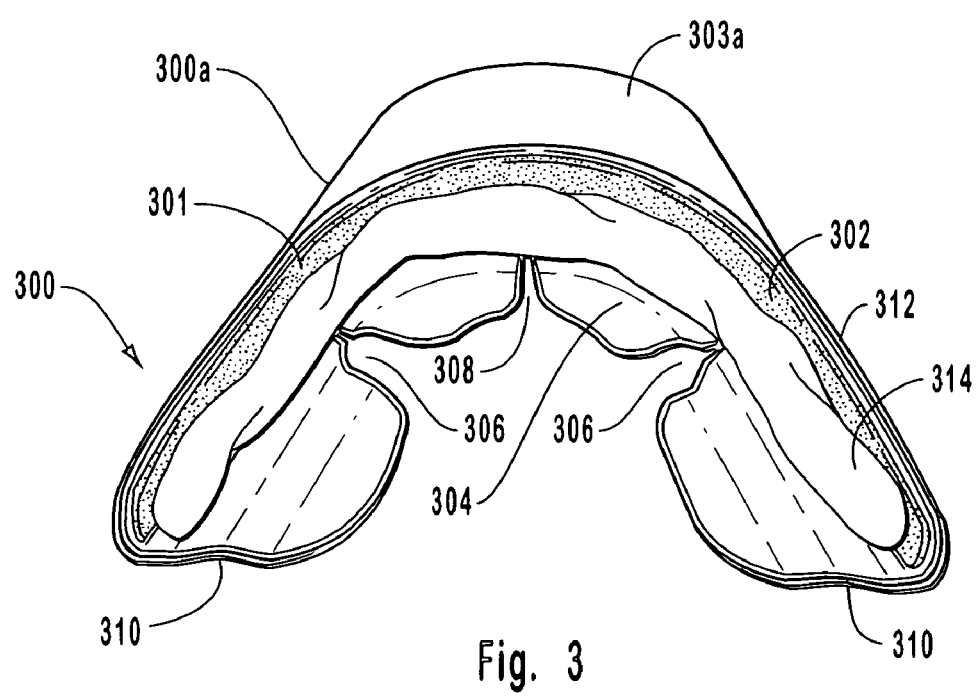
FIG. 3 is a perspective view of the device of FIG. 2 with a gel treatment composition placed within the tray shaped device.

FIG. 3 illustrates a tray-shaped dental treatment device 300 having a moisture-resistant barrier layer 312 having a front side wall 302 and a bottom wall 304. The device 300 is held within exoskeleton 300a which includes a handle 303a for grasping and placing the device on one's teeth. A substantially solid adhesive composition 301 is disposed adjacent to the front side wall 302. Tray-shaped dental treatment device 300 also includes a gel treatment composition 314 adjacent to at least one of the adhesive composition 301 or the barrier layer 312.

Bottom wall 304 includes notches 306 in the bottom wall 304 positioned so as to help the bottom wall 304 better conform to abrupt changes in the diameter of a person's teeth, particularly where the bicuspids and canines meet. Bottom wall 304 also includes an optional notch 308, which allows the tray-shaped dental treatment device 300 to more easily spread open or compress in the area of the incisors so as to more easily conform to differently-sized dental arches. The bottom wall 304 also includes two V-shaped indentations 310 configured to be inserted into the depressions typically found along the top surfaces of a person's left and right molars.

Figure 4A:
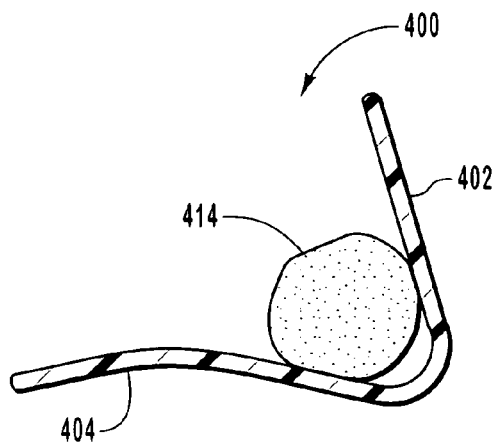
FIG. 4A is a cross sectional view of an exemplary tray-shaped dental treatment device with a gel treatment composition placed in the tray shaped device.
Figure 4B:
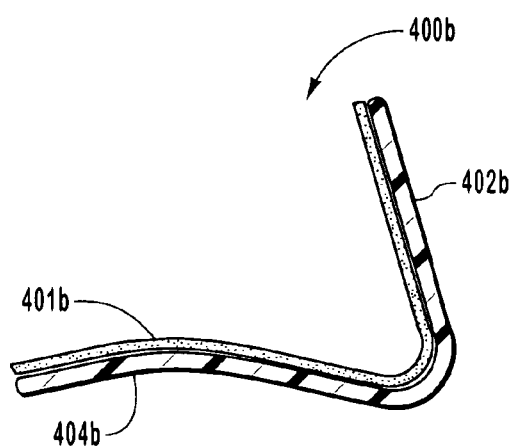
FIG. 4B is a cross sectional view of the exemplary tray-shaped dental treatment device of FIG. 2.
Figure 4C:
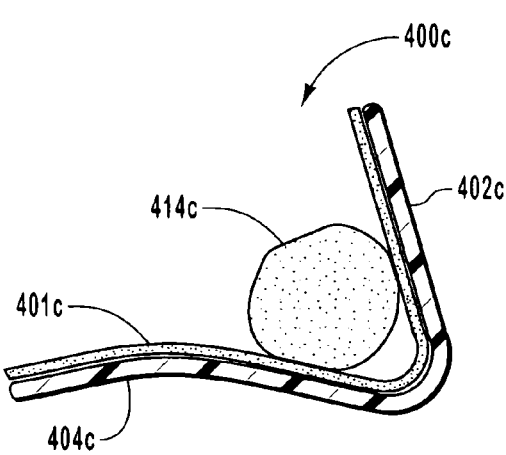
FIG. 4C is a cross sectional view of the exemplary tray-shaped dental treatment device of FIG. 3.
Figure 4D:
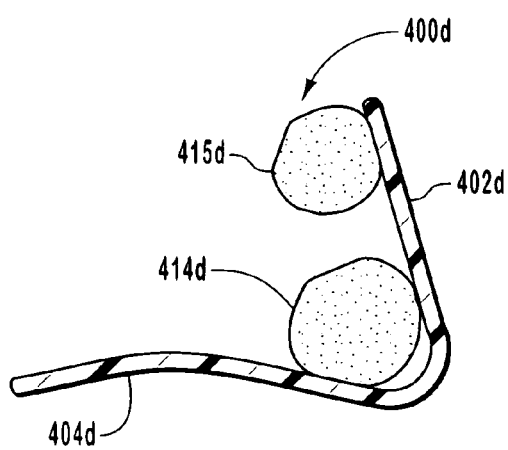
FIG. 4D is a cross sectional view of an exemplary tray-shaped dental treatment device with two separate gel treatment compositions placed in the tray shaped device.

FIGS. 4A–4D illustrate cross sections of various other exemplary tray-shaped dental treatment devices. FIG. 4A illustrates a cross section of a tray-shaped dental treatment device 400 including a front side wall 402 and a bottom wall 404. A gel treatment composition 414 is positioned adjacent to both the front side wall 402 and the bottom wall 404. FIG. 4B illustrates a cross section of a tray-shaped dental treatment device 400b including a front side wall 402b and a bottom wall 404b. A substantially solid adhesive composition 401b is positioned adjacent to both the front side wall 402b and the bottom wall 404b. FIG. 4C illustrates a cross section of a tray-shaped dental treatment device 400c including a front side wall 402c and a bottom wall 404c. A substantially solid adhesive composition 401c is positioned adjacent to both the front side wall 402c and the bottom wall 404c, while a gel treatment composition 414c is positioned adjacent to the substantially solid adhesive composition 401c. FIG. 4D illustrates a cross section of a tray-shaped dental treatment device 400d including a front side wall 402d and a bottom wall 404d. A gel treatment composition 414d is positioned adjacent to both the front side wall 402d and the bottom wall 404d, while a second gel treatment composition 415d is positioned adjacent to the front side wall 404d, near the top. Second gel treatment composition 415d may be a treatment composition intended to provide no treatment, and to contact the gums. Such a composition preferably contains no dental bleaching agent which otherwise may irritate the soft tissue surrounding the teeth (e.g. gingival tissue). Second gel treatment composition 415d reduces or prevents contact between gel treatment composition 414d and the person's soft tissue.

Figure 5:
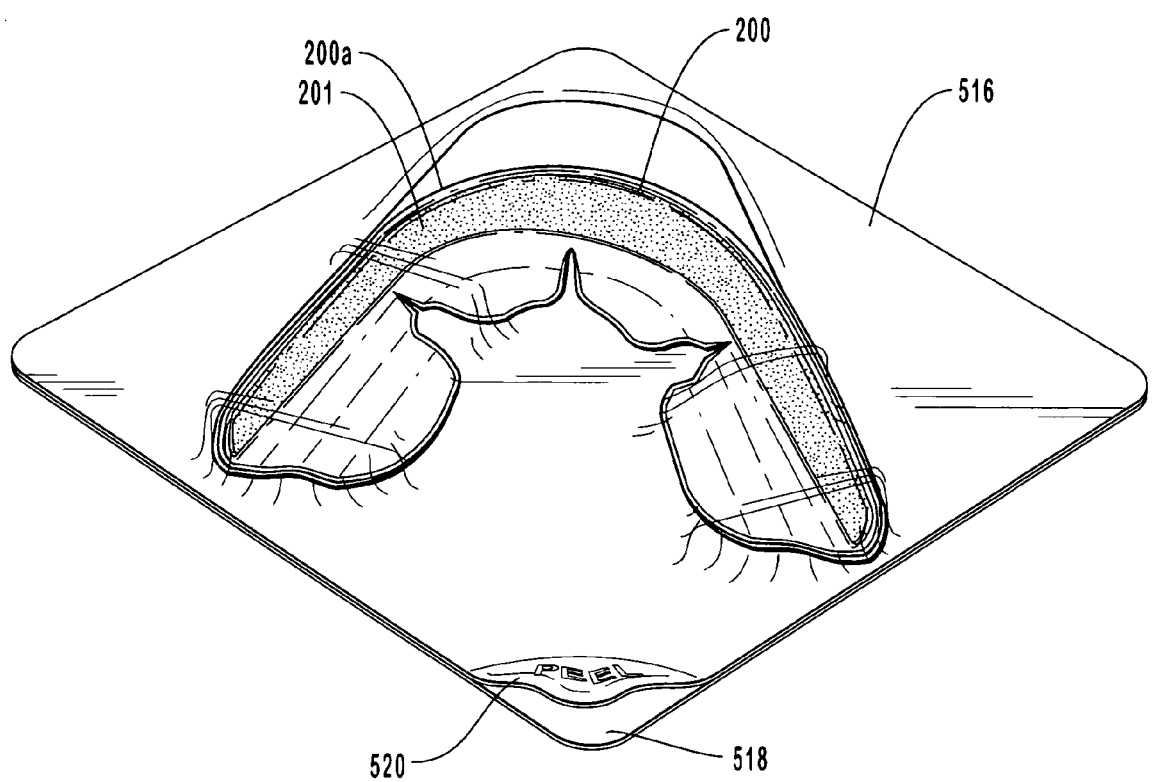
FIG. 5 illustrates an exemplary tray-shaped dental treatment device and associated exoskeleton contained within a sealed protective package having a peelable cover.

In order to protect a tray-shaped dental treatment device according to the invention from contaminants during storage and prior to use, the tray-shaped dental treatment device can be packaged within a sealed container or package. As illustrated in FIG. 5, the tray-shaped dental treatment device 200, along with an associated exoskeleton 200a can be sealed within a protective package 516 that includes a rigid support layer 518 and a peelable cover 520. Although illustrated with tray-shaped dental treatment device 200 and associated exoskeleton 200a, any embodiment of the tray-shaped dental treatment device with or without an associated exoskeleton can be sealed within a protective package. When it is desired to use the tray-shaped dental treatment device 200, the peelable cover 520 is removed and the bleaching device 200 is removed or separated from the support layer 518. In addition to, or instead of, the protective package 516, the tray-shaped dental treatment device 200 may alternatively include a removable protective layer (not shown) that is temporarily placed adjacent to the interior surface of the adhesive composition 201 and/or a gel or putty treatment composition. When it is desired to use the tray-shaped dental treatment device 200, the removable protective layer is removed so as to expose the interior surface of the adhesive composition 201 and/or other treatment composition. In addition, prior to using the tray-shaped dental treatment device 200, a gel or putty treatment composition may be applied to the inside of the device 200, as shown in FIG. 3, 4A, 4C, or 4D.

In general, the thickness of the adhesive composition layer and the barrier layer can be adjusted to yield a tray-shaped dental treatment device having a desired strength and flexibility. In order for the barrier layer to remain flexible so as to conform to a person's teeth, the barrier layer will generally have a thickness ranging from about 0.025 mm to about 1.5 mm. When present, the substantially solid adhesive composition will generally have a thickness ranging from about 0.1 mm to about 3 mm. The thickness of the adhesive composition can also be selected depending on the intended duration of each bleaching session. In general, increasing the thickness of the adhesive composition layer where the adhesive composition includes a dental bleaching agent will provide a longer or more sustained release of active dental bleaching agent. By way of example, for short wear times, the adhesive composition layer including a dental bleaching agent will preferably have a thickness ranging from about 0.1 mm to about 0.5 mm. For intermediate wear times, the adhesive composition layer including a dental bleaching agent will preferably have a thickness ranging from about 0.5 mm to about 2 mm. For professional use and for overnight bleaching, the adhesive composition layer having a dental bleaching agent will preferably have a thickness ranging from about 2 mm to about 3 mm.

III. Exemplary Methods of Making Tray-Shaped Dental Treatment Devices

According to one embodiment, the tray-shaped dental treatment device includes a moisture-resistant barrier layer having a front side wall and a bottom wall, a dental treatment composition, and at least one of the anatomical features discussed above to enhance the fit of the tray-shaped dental treatment device.

According to one method of manufacturing one exemplary device, an adhesive composition is made by first forming a flowable composition that is later dried to form a substantially solid adhesive composition. This may be performed by heating or otherwise causing one or more volatile solvents to be driven off by evaporation, thus leaving behind a substantially solid composition. The drying process may be performed before or after the adhesive composition is placed into contact with the barrier layer.

According to one embodiment, tray-shaped dental treatment devices can be made by spreading a flowable adhesive composition onto the surface of a large or continuous polymeric sheet. The polymeric sheet and adhesive composition are then placed into a forced air oven, other appropriate desiccation device, or allowed to dry in ambient conditions. Drying the sheet and adhesive composition drives off a substantial portion of the ethanol or other solvent used to form the flowable adhesive composition. Removal of the volatile solvent yields a substantially solid adhesive composition. Thereafter, individual tray-shaped dental treatment devices can be molded, such as by vacuum forming, pressing or stamping from the coated polymeric sheet and then separated into individual dental treatment devices suitable for placement over a person's teeth.

Alternatively, a flowable adhesive composition or a substantially solid adhesive composition can be molded or shaped into a desired tray-like configuration. Thereafter, a barrier layer may be attached or applied to an outer surface of the adhesive composition layer. In this embodiment, the barrier layer may initially comprise a flowable barrier material or precursor that is later cured or hardened, such as by removing a solvent by evaporation, by chemical or light curing, or by cooling a thermoplastic melt.

In yet another embodiment of the invention, a barrier layer having a front side wall and a bottom wall can be coated with a flowable adhesive composition. The adhesive composition is then heated together with the barrier layer or otherwise allowed to dry in order to form a substantially solid adhesive composition. This process can be performed during commercial manufacture of the tray-shaped dental treatment device or by an end user.

Sticky viscous gels, less viscous gels, and/or highly viscous putties may be manufactured separate from the barrier layer. They may be applied to the barrier layer or an adhesive composition prior to packaging, if desired. Alternatively, the tray-shaped dental treatment devices can be provided with a separate gel or putty which the end user may apply.

The tray-shaped dental treatment devices may be placed within an optional exoskeleton during the manufacturing process prior to packaging, if desired. Alternatively, the tray-shaped dental treatment devices may be provided with a separate exoskeleton, or without an exoskeleton, as desired.

IV. Exemplary Methods of Using Tray-Shaped Dental Treatment Devices

The tray-shaped dental treatment devices according to the invention can be designed to be worn for any desired time period. Increasing the concentration of dental bleaching agent in the treatment composition(s) generally reduces the bleaching time required to effect bleaching. Nevertheless, due to the extremely comfortable fit between the inventive tray-shaped dental treatment devices and the person's teeth, it is possible to wear such devices for extended periods of time in order to ensure more uniform bleaching. Especially with respect to tray-shaped dental treatment devices including a substantially solid adhesive composition layer, they may be designed to be worn while performing normal daily activities, such as talking, eating, drinking, smoking, coughing, smiling, frowning, grimacing, or while sleeping. This greatly decreases their intrusiveness into everyday activities compared to conventional bleaching strips, which do not reliably adhere to teeth, or intrusive bleaching devices such as large, bulky bleaching dental appliances.

Tray-shaped dental treatment devices according to the invention may be worn over a person's upper dental arch, lower dental arch, or both simultaneously. The ability to reliably and comfortably wear tray-shaped dental treatment devices over the upper and lower dental arches simultaneously is another departure from bleaching strips, which are not recommended for use in bleaching the upper and lower dental arches at the same time.

Figure 6A:
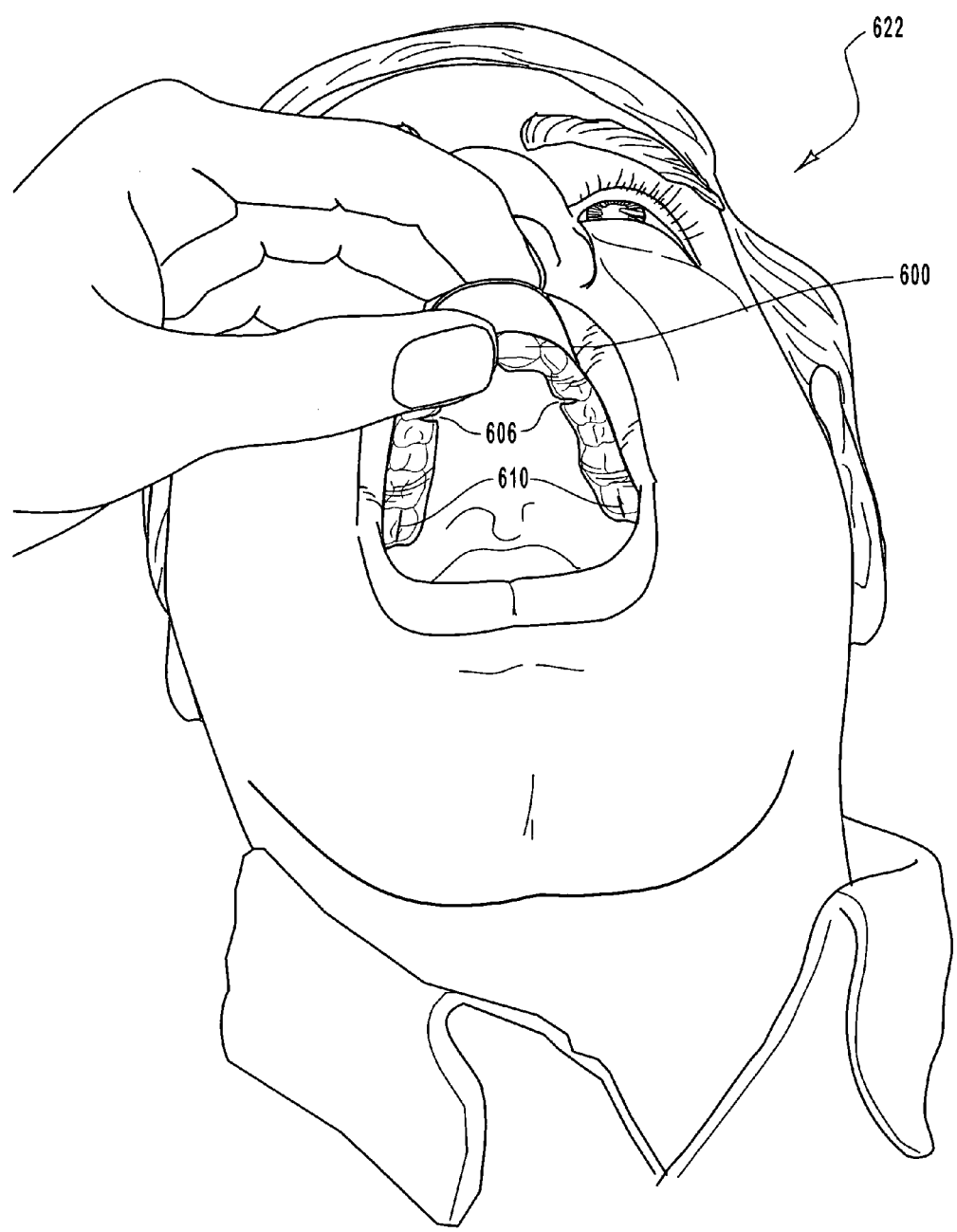
FIG. 6A illustrates a person placing a tray-shaped dental treatment device according to one embodiment of the invention over the upper dental arch.
Figure 6B:
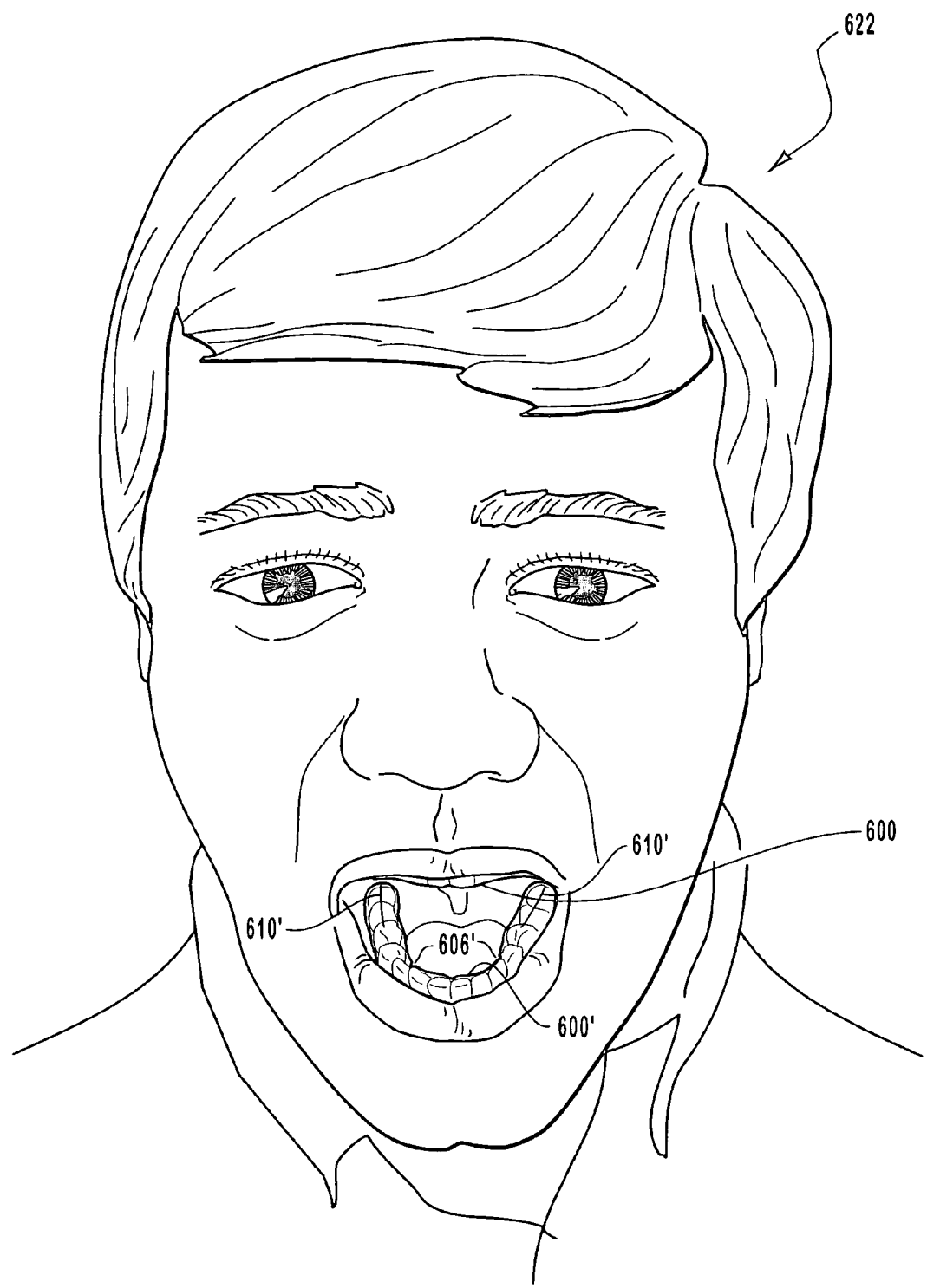
FIG. 6B illustrates a person having placed a tray-shaped dental treatment device according to one embodiment of the invention over the lower dental arch, with a tray-shaped dental treatment device already placed over the upper dental arch.

FIG. 6A illustrates a person 622 placing a tray-shaped dental treatment device 600 over the person's upper dental arch using an exoskeleton as a support. FIG. 6B illustrates the person 622 placing a tray-shaped dental treatment device 600' over the person's lower dental arch after having placed the tray-shaped dental treatment device 600 over the upper dental arch. It will be appreciated, however, that the tray-shaped dental treatment devices can be placed over a person's upper and lower dental arches in any desired order.

The tray-shaped dental treatment devices 600 and 600' include a plurality of notches 606 and 606', respectively, and V-shaped indentations 610 and 610', respectively, in the bottom wall. FIGS. 6A and 6B illustrate how the notches 606, 606' in the bottom wall help the bottom wall better conform to abrupt changes in the diameter of a person's teeth where the bicuspids and canines meet.

Figure 7A:
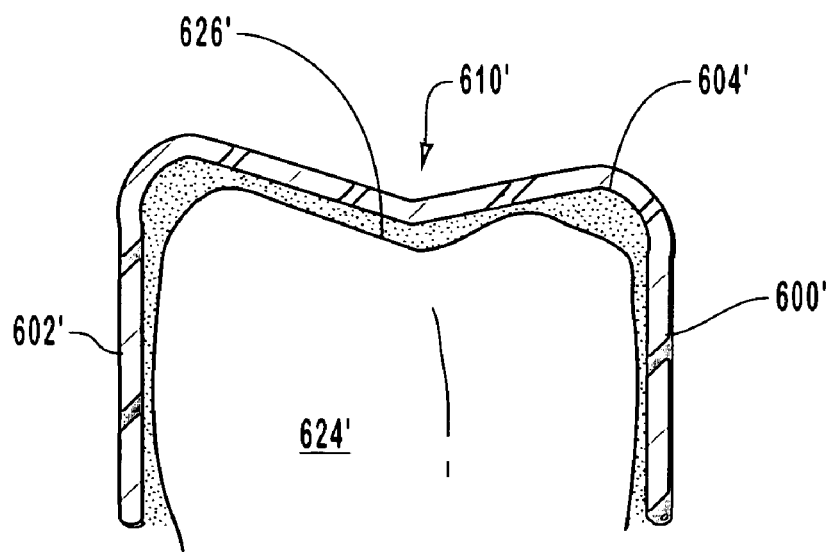
FIG. 7A is a close up cross sectional view of the exemplary tray-shaped dental treatment device of FIG. 6B placed over a persons lower dental arch showing how the V-shaped indentation in the bottom wall is configured for insertion into the depression of a person's molars.

FIG. 7A is a close up cross sectional view illustrating how the V-shaped indentation 610' in the bottom wall 604' of tray-shaped dental treatment device 600' is configured for insertion into the depression in the lower molar 624'. As seen, molar 624' includes a depression 626' into which V-shaped indentation 610' is configured to be inserted. This results in better conformity between the tray-shaped dental treatment device 600' and the molar 624', even when downward pressure is applied to the bottom wall 604'.

In the absence of such indentations, the bottom wall 604' of the treatment device 600' may have a tendency to span the molar 624' like a bridge between the generally higher outer edges, thereby leaving a gap between the bottom wall 604' and the surface of the molar 624' between the outer edges. Permitting such a gap may inhibit or prevent bleaching of the depressed molar surfaces. Moreover, a bottom wall 604' that is stretched between the outer surfaces so as to leave a gap over the molar depressions may result in inadvertent dislodgment of the treatment device 600' when the upper and lower molars are brought together. For example, if the bottom wall 604' of a treatment device 600' is pushed into the molar depression 626' by the opposing molars, the front and/or bottom side walls 602' and 604', respectively, may be pulled down across the tooth surfaces to compensate for this effective lengthening of the bottom wall 604' in the vicinity of the patient's molars.

Figure 7B:
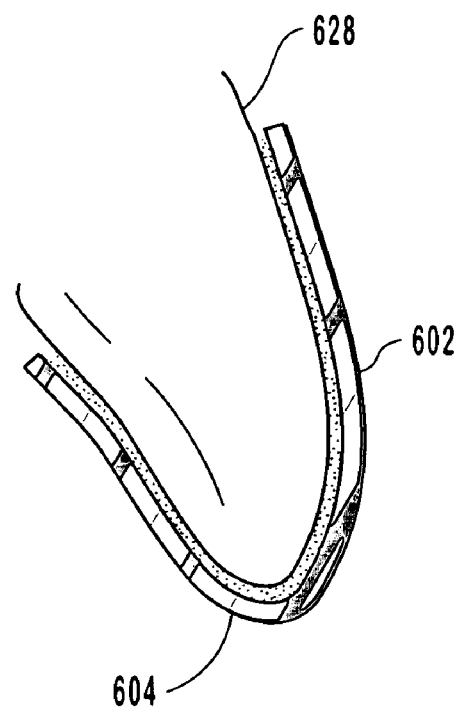
FIG. 7B is a close up cross sectional view of the exemplary tray-shaped dental treatment device of FIG. 6A placed over a person's upper dental arch showing how the curvature of the front side wall and bottom wall account for flaring of a person's incisors.

FIG. 7B is a close up cross sectional view illustrating how the curvature of the front side wall 602 and bottom wall 604 account for flaring of the person's incisors 628. A typical person's incisors are not vertical. Rather, they typically flare outwards slightly. The front side wall 602 and bottom wall 604 may have different radii in order to compensate for the general flaring out of a person's incisors toward the incisal edges. Due to such flaring the diameter of a person's dental arch at the incisal edges is generally greater than the diameter at the gingival margin. Thus the part of the treatment device 600 corresponding to the incisal edges near a person's incisor 628 may advantageously have a larger radius than the part of the treatment device 600 corresponding to the gingival margin. This helps provide for a better fit of the treatment device 600 over a person's incisors 628.

To remove the tray-shaped dental treatment device, a user can pry open a corner of the barrier layer using a fingernail or rigid tool and then pull the remainder off. Any residual adhesive composition or gel or putty treatment composition that remains adhered to the person's teeth can be removed by washing or flushing water over the person's teeth, and/or by brushing. Although the adhesive compositions are very adhesive to teeth when protected from excessive moisture, they can be formulated to quickly breakdown and dissolve when flushed with excess water and/or by gentle mechanical action (e.g., brushing).

The tray-shaped dental treatment devices can be worn for as little as a few minutes and as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours.

Bleaching sessions may be repeated as many times as are needed to obtain a desired degree of whitening. In some cases, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

V. Dental Bleaching Kits

For convenience of use, multiple tray-shaped dental treatment devices may be packaged together and sold as a kit. In one embodiment, the number treatment devices provided with each kit will equal the number of sessions that represent a prescribed bleaching regimen.

To efficiently utilize the space within a kit package, multiple tray-shaped dental treatment devices can be stacked or interested together. The devices can be sealed collectively or individually as desired. A protective package 516 is depicted in FIG. 5. The bleaching devices may optionally contain a removable protective layer on an interior surface to protect the adhesive composition from contamination or moisture.

It is within the scope of the invention to provide exoskeletons, barrier layers, gel or putty treatment compositions, and/or adhesive compositions that are initially separate and that are brought together by the end user. For example, the adhesive composition may be a dry insert that is placed into a tray-like barrier layer, with or without actually adhering the adhesive composition to the barrier layer. Alternatively, a flowable adhesive composition can be placed within a tray-like barrier layer and allowed to dry prior to placement of the finished tray-shaped dental treatment device over the person's teeth.

VI. Examples of the Preferred Embodiments

Following is an example of a tray-shaped dental treatment device that has been formulated and manufactured according to the invention. Additional examples of treatment compositions and barrier layers that may be used are disclosed in U.S. patent application Ser. No. 10/446,235, filed May 27, 2003 and titled TRAY-LIKE DENTAL BLEACHING DEVICES HAVING A BARRIER LAYER AND A SUBSEQUENTLY SOLID BLEACHING COMPOSITION, hereby incorporated by reference with respect to examples of barrier layers and treatment compositions. The exemplary formulations and manufacturing conditions are given by way of example, and not by limitation, in order to illustrate tray-shaped dental treatment devices that have been found to be useful for bleaching a person's teeth. Unless otherwise indicated, all percentages are by weight.

EXAMPLE 1

An initially flowable adhesive composition suitable for use in manufacturing a substantially solid adhesive composition was formed by mixing together the following components:

| | |
|---|---|
| Ethanol | 31.95% |
| Water | 10% |
| Polyvinyl Pyrrolidone (M.W. = 1.3 million) | 27% |
| Polyvinyl Pyrrolidone (M.W. of about 60,000) | 10% |
| Sodium Laurel Sulfate | 0.5% |
| Glycerine | 15% |
| Sucralose 25% solution | 0.5% |
| Peach Flavor | 4% |
| Potassium Nitrate | 0.8% |
| Sodium Fluoride | 0.25% |

The resulting adhesive composition was spread over the surface of a large flat sheet formed of 80% ethyl vinyl acetate and 20% polypropylene. The EVA/PP sheet had a thickness of about 0.15 mm. The adhesive composition was spread using a skreeding device. The coated sheet was heated in a forced air oven until the adhesive composition dried. The coated sheet was removed from the oven and inspected. The adhesive composition had dried sufficiently so as to form a substantially solid layer on the surface of the polymer sheet. The adhesive composition was dry to the touch, but became very sticky when touched by a wet object. After drying, the adhesive composition film was reduced to approximately one-third of its original thickness when wet.

The coated sheet was thermoformed into tray-shaped devices with the dry adhesive composition on the inside surface of the devices. Individual tray-shaped devices were cut out using dye cutting tools. A laser could alternatively be used for cutting. The tray-shaped devices included a front side wall, a bottom wall, a plurality of notches formed in the bottom wall so as to help the bottom wall better conform to abrupt changes in the diameter of a person's teeth, particularly where the bicuspids and canines meet, two V-shaped indentations in the bottom wall configured to be inserted into the depression typically found in a persons left and right molars, and a curvature of the front side wall and bottom wall that accounts for typical flaring of a person's incisors.

A bleaching gel treatment composition for use with the tray-shaped devices was prepared by mixing together the following components:

| | |
|---|---|
| Water | 22.5% |
| EDTA Disodium | 0.1% |
| Carbamide Peroxide | 18.5% |
| Sucralose 25% solution | 0.75% |
| Glycerine | 41.6% |
| Carbopol 974 | 5.3% |
| Sodium Hydroxide 50% solution | 2.25% |
| Polyvinyl Pyrrolidone (M.W. = 1.3 million) | 2% |
| Carboxymethyl Cellulose | 4% |
| Watermelon Flavor | 3% |

The tray-shaped devices were placed in a holding device, and a bead of bleaching gel treatment composition was spread along the front side wall of the bleaching devices. Each tray-shaped device was then transferred to an exoskeleton.

The tray-shaped devices were tested by placing them over a person's teeth. The residual saliva present on the tooth surfaces moistened the exposed surface of the adhesive composition and caused it to become sticky and very adhesive to teeth almost immediately. The tray-shaped devices were pressed against the teeth, which caused them to conform to the natural irregularities of the dental arch and adhere firmly against the teeth. The plurality of notches formed in the bottom wall helped the bottom wall better conform to abrupt changes in the diameter of a person's teeth, particularly where the bicuspids and canines meet. The two V-shaped indentations in the bottom wall were received within the depression in the left and right molars, and the curvature of the front side wall and bottom wall resulted in a good fit against the person's outwardly flared incisors.

The tray-shaped devices were worn for varying time periods ranging from several minutes to several hours without becoming dislodged. In some cases a noticeable bleaching effect was detected after just one bleaching session (e.g., a 2-hour bleaching session). In all cases, noticeable bleaching was detected after 1–3 bleaching sessions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental treatment system for use in applying a treatment composition to a person's teeth, comprising:

a moisture-resistance barrier layer having a front side wall and a bottom wall, and that is adapted to be worn over at least a portion of a person's upper or lower dental arch without requiring customization prior to wearing, the barrier layer comprising a thin-walled, flexible membrane material that is adapted to at least partially conform to the person's teeth when placed over a patient's teeth to apply the treatment composition;

said barrier layer comprising one or more anatomical features that facilitate the ability of the barrier to conform to the patient's teeth when worn for treatment;

a support skeleton positioned adjacent to the barrier layer prior to placement over the patient's teeth so as to maintain the thin-walled flexible membrane material in a tray-like configuration to facilitate placement of the barrier layer when forming the treatment tray by its placement over the person's teeth; and a dental treatment composition placed onto the barrier layer prior to its placement over the patient's teeth.

2. A tray-shaped dental treatment device as recited in claim 1, wherein said support skeleton comprises an exoskeleton having a tray-like configuration configured to receive said moisture-resistant barrier layer.

3. A tray-shaped dental treatment device as recited in claim 2, wherein said exoskeleton includes a handle.

4. A tray-shaped dental treatment device as recited in claim 1, wherein said dental treatment composition comprises at least one of a sticky viscous gel, a less viscous gel, a highly viscous putty, or a substantially solid composition.

5. A tray-shaped dental treatment device as recited in claim 4, wherein the dental treatment composition includes at least one tissue adhesion agent.

6. A tray-shaped dental treatment device as recited in claim 5, wherein said dental treatment composition further includes at least one active agent.

7. A tray-shaped dental treatment device as recited in claim 6, said active agent comprising at least one of a dental bleaching agent, a desensitizing agent, a remineralizing agent, an antimicrobial agent, an antiplaque agent, an antitartar agent, or another medicament.

8. A tray-shaped dental treatment device as recited in claim 5, said tissue adhesion agent comprising polyvinyl pyrrolidone.

9. A tray-shaped dental treatment device as recited in claim 5, said tissue adhesion agent comprising at least one of carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, and protein.

10. A tray-shaped dental treatment device as recited in claim 5, said tissue adhesion agent having a concentration in a range of about 10% to about 90% by weight of said treatment composition.

11. A tray-shaped dental treatment device as recited in claim 5, said tissue adhesion agent having a concentration in a range of about 20% to about 80% by weight of said treatment composition.

12. A tray-shaped dental treatment device as recited in claim 5, said tissue adhesion agent having a concentration in a range of about 40% to about 75% by weight of said treatment composition.

13. A tray-shaped dental treatment device as recited in claim 5, wherein the treatment composition comprises a substantially solid adhesive composition and at least one of a sticky viscous gel, a less viscous gel, or a highly viscous putty adjacent to at least one of said adhesive composition or said barrier layer.

14. A tray-shaped dental treatment device as recited in claim 1, wherein said device is contained within a sealed package prior to use.

15. A dental treatment system for use in applying a treatment composition to a person's teeth, comprising:
 a moisture-resistant barrier layer having a front side wall and a bottom wall, and that is adapted to be worn over at least a portion of a person's upper or lower dental arch without requiring customization prior to wearing, the barrier layer comprising a thin-walled, flexible membrane material that is adapted to at least partially conform to the person's teeth when placed over a patient's teeth to apply the treatment composition;
 said barrier layer comprising one or more anatomical features that facilitate the ability of the barrier to conform to the patient's teeth when worn for treatment;
 a support skeleton positioned adjacent to the barrier layer prior to placement over the patient's teeth so as to maintain the thin-walled flexible membrane material in a tray-like configuration to facilitate placement of the barrier layer when forming the treatment tray by its placement over the person's teeth; and
 a substantially solid adhesive composition that has increased adhesiveness to teeth when moistened with saliva or water, said adhesive composition including;
  at least one active agent; and
  at least one tissue adhesion agent that contributes or provides increased adhesiveness to oral tissue when moistened with saliva; and
  at least one of a sticky viscous gel, a less viscous gel, or a highly viscous putty adjacent to at least one of said barrier layer or said adhesive composition.

16. A tray-shaped dental treatment device as recited in claims 1 or 15, wherein said one or more anatomical features comprise a plurality of cuts positioned so as to help said bottom wall better conform to abrupt changes in the diameter of a person' teeth where the bicuspids and canines meet, and wherein each of said cuts comprises a notch.

17. A tray-shaped dental treatment device as recited in claims 1 or 15, wherein said one or more anatomical features comprises a notch in said bottom wall so as to help said tray-shaped dental treatment device to more easily spread open or compress in the area of a person's incisors.

18. A tray-shaped dental treatment device as recited in claims 1 or 15, wherein said one or more anatomical features comprises at least one V-shaped or U-shaped indentation in said bottom wall configured to be inserted into the depression typically found along the top surfaces of a person's molars.

19. A tray-shaped dental treatment device as recited in claims 1 or 15, wherein said one or more anatomical features comprise radii of curvature on the front side wall and bottom wall that account for typical flaring of a patient's incisors.

20. A tray-shaped dental treatment device as recited in claim 15, wherein said support skeleton comprise an exoskeleton having a tray-like configuration configured to receive said moisture-resistant barrier layer.

21. A tray-shaped dental treatment device as recited in claim 15, said barrier layer comprising a mixture of ethyl vinyl acetate and polypropylene.

22. A tray-shaped dental treatment device as recited in claim 21, said barrier layer comprising up to 50% polypropylene by weight.

23. A tray-shaped dental treatment device as recited in claim 21, said barrier layer comprising about 5% to about 40% polypropylene by weight.

24. A tray-shaped dental treatment device as recited in claim 21, said barrier layer comprising about 10% to about 30% polypropylene by weight.

25. A tray-shaped dental treatment device as recited in claim 15, said barrier layer comprising at least one polyolefin.

26. A tray-shaped dental treatment device as recited in claim 25, said polyolefin comprising at least one of polyethylene, high density polyethylene, low density polyethylene, ultra-low density polyethylene, polypropylene, or polytetrafluoroethylene.

27. A tray-shaped dental treatment device as recited in claim 15, said barrier layer comprising at least one of wax, metal foil, paraffin, ethylene-vinyl acetate copolymer, ethylene-vinyl alcohol copolymer, polycaprolactone, polyester, polycarbonate, polyurethane, polyamide, or polyesteramide.

28. A tray-shaped dental treatment device as recited in claim 15, wherein said baffler layer has a cross-sectional thickness in a range of about 0.025 mm to about 1.5 mm.

29. A tray-shaped dental treatment device as recited in claim 15, wherein said barrier layer is sized and configured so as to approximately terminate at or near a person's gingival margin when said tray-shaped dental treatment device is in use.

30. A tray-shaped dental treatment device as recited in claim 15, said at least one sticky viscous gel, less viscous gel, or highly viscous putty includes a dental bleaching agent.

31. A tray-shaped dental treatment device as recited in claim 30, said dental bleaching agent comprising at least one of carbamide peroxide, metal peroxide, percarbonate, perborate, peroxy acid, peroxy acid salt, chlorite, or hypochlorite.

32. A tray-shaped dental treatment device as recited in claim 30, said dental bleaching agent having a concentration in a range of about 5% to about 80% by weight of said at least one sticky viscous gel, less viscous gel, or highly viscous putty.

33. A tray-shaped dental treatment device as recited in claim 30, said dental bleaching agent having a concentration in a range of about 10% to about 60% by weight of said at least one sticky viscous gel, less viscous gel, or highly viscous putty.

34. A tray-shaped dental treatment device as recited in claim 30, said dental bleaching agent having a concentration in a range of about 20% to about 50% by weight of said at least one sticky viscous gel, less viscous gel, or highly viscous putty.

* * * * *

UNITED STATES PATENT AND TRADEMARK OFFICE
CERTIFICATE OF CORRECTION

PATENT NO.        : 7,059,858 B2
APPLICATION NO. : 10/783597
DATED             : June 13, 2006
INVENTOR(S)       : McLean et al.

It is certified that error appears in the above-identified patent and that said Letters Patent is hereby corrected as shown below:

Column 4
Line 8, after "adhesive" remove ":"

Column 5
Line 59, change "tray shaped" to --tray-shaped--

Column 6
Line 6, change "persons" to --person's--

Column 15
Line 62, after "the number" insert --of--

Column 16
Line 59, change "skreeding" to --screeding--

Column 17
Line 11, change "persons" to --person's--

Column 18
Line 1, change "moisture-resistance" to --moisture-resistant--

Column 19
Line 58, change "compromise" to --comprises--

Column 20
Line 27, change "baffler" to --barrier--

Signed and Sealed this

Fifth Day of December, 2006

JON W. DUDAS
*Director of the United States Patent and Trademark Office*